US012633412B2

(12) United States Patent
Kawagishi

(10) Patent No.: US 12,633,412 B2
(45) Date of Patent: May 19, 2026

(54) INFORMATION PROCESSING APPARATUS, INFORMATION PROCESSING METHOD AND STORAGE MEDIUM

(71) Applicants: CANON KABUSHIKI KAISHA, Tokyo (JP); CANON MEDICAL SYSTEMS CORPORATION, Tochigi (JP)

(72) Inventor: Masami Kawagishi, Kanagawa (JP)

(73) Assignees: CANON KABUSHIKI KAISHA, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 771 days.

(21) Appl. No.: 18/061,511

(22) Filed: Dec. 5, 2022

(65) Prior Publication Data

US 2023/0178240 A1    Jun. 8, 2023

(30) Foreign Application Priority Data

Dec. 7, 2021    (JP) ................................. 2021-198306

(51) Int. Cl.
*G16H 50/20*        (2018.01)
*G06T 7/00*         (2017.01)
*G06T 7/11*         (2017.01)

(52) U.S. Cl.
CPC ........... *G16H 50/20* (2018.01); *G06T 7/0012* (2013.01); *G06T 7/11* (2017.01)

(58) Field of Classification Search
CPC ........ G16H 50/20; G16H 30/40; G16H 30/20; G16H 50/30; G16H 15/00; G06N 20/00;
(Continued)

(56) References Cited

U.S. PATENT DOCUMENTS 9,436,915 B2 *   9/2016   Kawagishi ............. G16H 50/20
9,542,594 B2 *   1/2017   Umeda ................... G06V 20/30
(Continued)

FOREIGN PATENT DOCUMENTS

JP        2010-200840 A      9/2010
JP         2015011557 A      1/2015

OTHER PUBLICATIONS

Selvaraju, R et al., "Grad-CAM: Why did you say that? Visual Explanations from Deep Networks via Gradient-based Localization" CoRR, arXiv:1610.02391v4 (Dec. 2019) pp. 1-23, http://arxiv.org/abs/1610.02391.

(Continued)

*Primary Examiner* — Courtney Joan Nelson
(74) *Attorney, Agent, or Firm* — Carter, DeLuca & Farrell LLP

(57)        ABSTRACT

An information processing apparatus for making inferences using image data, comprising: a first inference unit configured to perform a first inference using the image data to obtain a first inference result; at least one second inference unit configured to make a second inference different from the first inference, using the image data, to obtain a second inference result; an information-of-interest acquisition unit configured to obtain a first region of interest which is region information focused in the image data, in the obtainment of the first inference result, and to obtain a second region of interest which is region information focused upon in the image data, in the obtainment of the second inference result; and a determination unit configured to determine relatedness of the first region and the second region of interest from an inclusion relation of the first region and the second region of interest in the image data.

22 Claims, 8 Drawing Sheets

(58) Field of Classification Search
CPC ...... G06N 3/0464; G06N 3/02; G06T 7/0012;
G06T 2207/30004; G06T 2210/41; G06T
2207/20076; G06T 7/11; A61B 1/000096;
A61B 5/0013; A61B 5/00
See application file for complete search history.

(56) References Cited

U.S. PATENT DOCUMENTS

| | | | | |
|---|---|---|---|---|
| 9,734,299 | B2 | 8/2017 | Yakami et al. | |
| 9,940,715 | B2 | 4/2018 | Fujimoto et al. | |
| 11,527,328 | B2 * | 12/2022 | Kikuchi ................. | G16H 30/40 |
| 2016/0357925 | A1 | 12/2016 | Kawagishi et al. | |
| 2020/0342266 | A1 * | 10/2020 | Nitta ...................... | G06V 10/82 |
| 2021/0027465 | A1 * | 1/2021 | Kawagishi ............. | G06V 10/25 |

OTHER PUBLICATIONS

Tachibana, Y. et al., "Development of Useful Pretreatment Software for the Use of Convolutional Deep Neural Networks in Diagnostic Imaging" 36th Annual Meeting of the Japanese Society of Medical Imaging Technology (Jul. 2017) pp. 1-2, with English translation.
Xu, K. et al., "Show, Attend and Tell: Neural Image Caption Generation with Visual Attention" CoRR, arXiv:1502.03044v3 (Apr. 2016) pp. 1-22, http://arxiv.org/abs/1502.03044.
Notice of Reasons for Refusal issued by the Japanese Patent Office on Sep. 30, 2025 in corresponding JP Patent Application No. 2021-198306, with English translation.

* cited by examiner

(A) FIRST INFERENCE UNIT (B) (2-K)TH INFERENCE UNIT

INFORMATION PROCESSING APPARATUS, INFORMATION PROCESSING METHOD AND STORAGE MEDIUM

BACKGROUND OF THE INVENTION

Field of the Invention

The disclosure in the present specification relates to an information processing apparatus, an information processing method, and a storage medium.

Description of the Related Art

Techniques are known in which information that serves as inference clues is presented for an inference result that is to be calculated, by machine learning (inference means), on the basis of input information.

Japanese Patent Application Publication No. 2010-200840 discloses a technique in which inferences are made using all of input information, and inferences are also made using some input information, the influence exerted on inference results is determined on the basis of differences in inference probabilities, and there is presented information, from among the input information, that has been deemed to be negative to the inference result.

Ramprasaath et al., "Grad-CAM: Why did you say that? Visual Explanations from Deep Networks via Gradient-based Localization", CoRR, arXiv (http://arxiv.org/abs/1610.02391), 2016, discloses a technique in which inferences on an input image are made by deep learning, after which a portion of significant contribution (gradient) to the inference result is regarded as an important site for inference, and a color map is displayed superimposed on the image.

It is conceivable herein to make multiple inferences from the same input information. If relatedness between multiple inference results can be grasped in such a case, then other inference results can be presented as reference information for one inference result. For instance there can be presented another inference result strongly related to a main inference result, in other words, another inference result serving as a basis for the main inference result.

However, conventional techniques did not allow grasping relatedness between multiple inference results that derive from identical input information.

SUMMARY OF THE INVENTION

An object of the present disclosure is to acquire relatedness between multiple inference results in a case where multiple inferences are made from identical input information.

The first aspect of the present disclosure is an information processing apparatus for making inferences using image data, comprising: a first inference unit configured to perform a first inference using the image data to obtain a first inference result; at least one second inference unit configured to make a second inference different from the first inference, using the image data, to obtain a second inference result; an information-of-interest acquisition unit configured to obtain a first region of interest which is region information focused in the image data, in obtainment of the first inference result, and to obtain a second region of interest which is region information focused upon in the image data, in obtainment of the second inference result; and a determination unit configured to determine relatedness of the first region of interest and the second region of interest from an inclusion relation of the first region of interest and the second region of interest in the image data.

The second aspect of the present disclosure is an information processing apparatus for making inferences using image data, comprising: a first inference unit configured to perform a first inference using the image data to obtain a first inference result; at least one second inference unit configured to make a second inference different from the first inference, using the image data, to obtain a second inference result; an information-of-interest acquisition unit configured to obtain a first region of interest which is region information focused upon in the image data, in obtainment of the first inference result, and to obtain a second region of interest which is region information focused in the image data, in obtainment of the second inference result; and a determination unit configured to determine relatedness between pixels that constitute the first region of interest and pixels that constitute the second region of interest, in the image data.

The third aspect of the present disclosure is an information processing method for making an inference using image data, comprising: a first inference step of making a first inference using the image data to obtain a first inference result; at least one second inference step of making a second inference different from the first inference, using the image data, to obtain a second inference result; an information-of-interest acquisition step of obtaining a first region of interest which is region information focused in the image data, in obtainment of the first inference result, and obtaining a second region of interest which is region information focused upon in the image data, in obtainment of the second inference result; and a determination step of determining relatedness between the first region of interest and the second region of interest, from an inclusion relation of the first region of interest and the second region of interest.

The fourth aspect of the present disclosure is an information processing method for making an inference using image data, comprising: a first inference step of making a first inference using the image data to obtain a first inference result; at least one second inference step of making a second inference different from the first inference, using the image data, to obtain a second inference result; an information-of-interest acquisition step of obtaining a first region of interest which is region information focused in the image data, in obtainment of the first inference result, and obtaining a second region of interest which is region information focused upon in the image data, in obtainment of the second inference result; and a determination step of determining relatedness between the first region of interest and the second region of interest, from an inclusion relation of the first region of interest and the second region of interest.

According to the present disclosure, the relatedness between multiple inference results can be presented by determining the relatedness of information focused upon in the obtainment of the multiple inference results from the same input information. Further, based on the relatedness, one inference result can be presented as a reference information to another inference result.

Further features of the present invention will become apparent from the following description of exemplary embodiments with reference to the attached drawings.

BRIEF DESCRIPTION OF THE DRAWINGS

FIG. 6 is a diagram illustrating an example of processing flow performed by an information processing apparatus;

DESCRIPTION OF THE EMBODIMENTS

Embodiments for implementing the present invention will be explained next with reference to accompanying drawings. However, the features described in the embodiments are merely illustrative in nature, and the technical scope of the information processing apparatus disclosed in the present specification is defined by the claims, and is not limited by the individual embodiments below.

The disclosure of the present specification is not limited to the following embodiments, and can accommodate various alterations (including organic combinations of embodiments) on the basis of the gist of the disclosure of the present specification, such alterations not being meant to be excluded from the scope of the disclosure of the present specification. That is, all features arrived at by combining the below-described embodiments and variations thereof are likewise encompassed by the embodiments in the disclosure of the present specification.

Embodiment 1

The information processing apparatus in Embodiment 1 acquires a medical image as input information, extracts information of interest that is an inference clue for inference results by respective inference means that utilize deep learning, determines relatedness of the inference result on the basis of the information of interest, and presents the relatedness as reference information. In the present embodiment the medical image is a three-dimensional chest X-ray CT image, and there are inferred a lung disease name and a plurality of image findings. Needless to say, the targets for inference are not limited to these, which are all merely examples for explaining processes in the information processing apparatus. For instance the type of the medical image may be an X-ray CT image, a plain X-ray image (Roentgen image), an MRI image, a PET image, a SPECT image or an ultrasound image. The organ and site to be diagnosed is likewise arbitrary.

Figure 1:
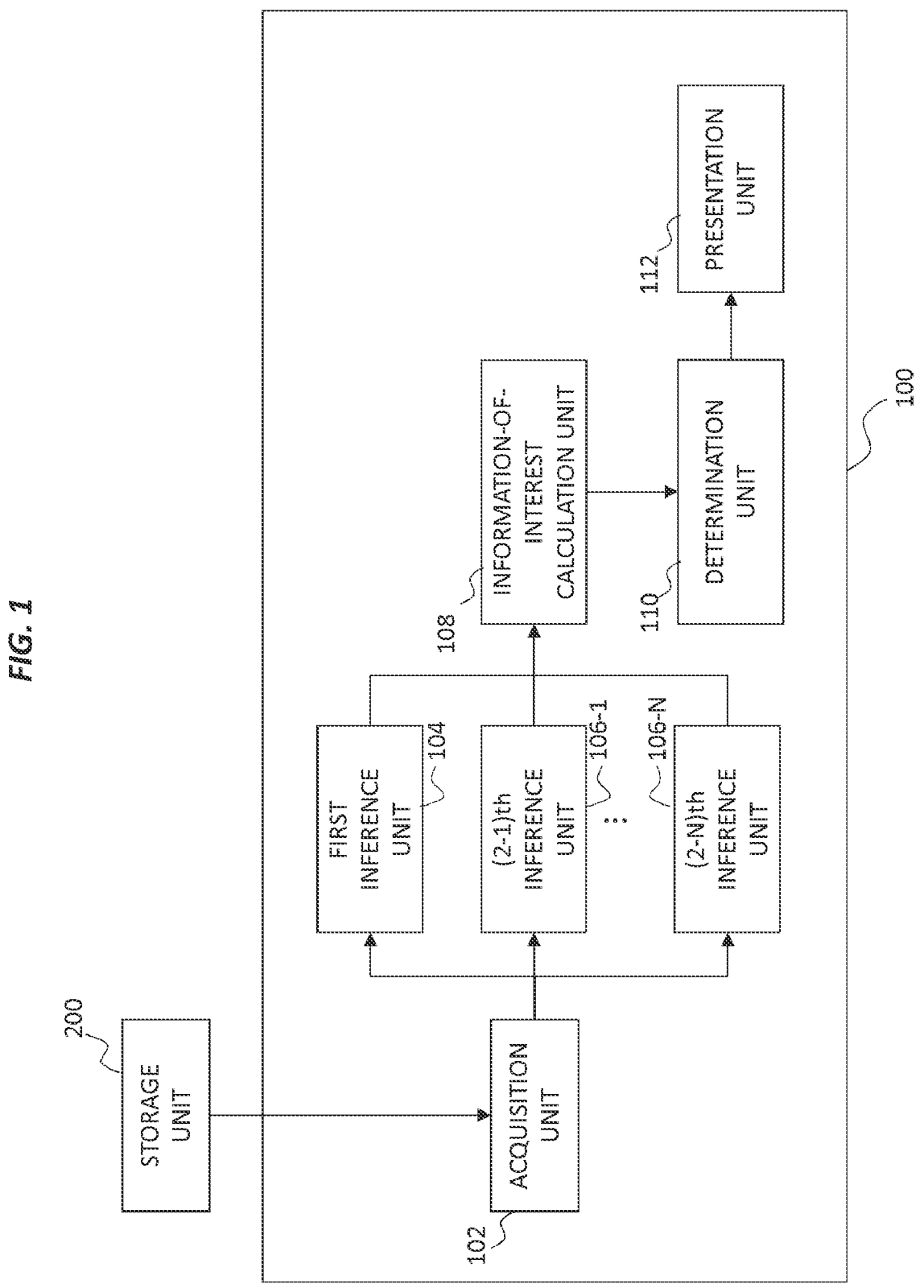
FIG. 1 is a diagram illustrating an example of the functional configuration of an information processing apparatus.

FIG. 1 is a diagram illustrating an example of the functional configuration of an information processing apparatus 100 according to Embodiment 1. The information processing apparatus 100 of the present embodiment is connected to a storage unit 200 that holds medical images. Needless to say, the storage unit 200 may hold information other than medical images. The storage unit 200 may be in the form of a PACS, an electronic medical record or an interpretation report, such that image information is acquired in response to a request from the information processing apparatus 100.

The information processing apparatus 100 is provided with an acquisition unit 102, a first inference unit 104, second inference units 106-1 to 106-N, an information-of-interest calculation unit 108, a determination unit 110 and a presentation unit 112.

The acquisition unit 102 issues a request to the storage unit 200, and acquires input information. The input information of the present embodiment is image data, in particular three-dimensional chest X-ray CT image data.

The first inference unit 104 makes a first inference on the basis of the input information to obtains a first inference result. The second inference units 106-1 to 106-N make a second inference on the basis of the input information, to obtain (2-1)th to (2-N)th inference results, respectively. The second inference units 106-1 to 106-N may be collectively referred to as second inference units 106 when the units need not be distinguished from each other. The number N of the second inference units 106 may be any number equal to or greater than 1, but ordinarily N takes on a value of 2 or larger.

In the calculation of the first inference result, the information-of-interest calculation unit 108 calculates first information of interest, which is information focused upon in the input information. In the calculation of the (2-1)th to (2-N)th inference results, the information-of-interest calculation unit 108 calculates (2-1)th to (2-N)th information items of interest which are pieces of information focused upon in the input information. The first and second information of interest may be obtained by other than calculation. The term information of interest in the present embodiment denotes information on a region of interest in the input information (image data), in the calculation of an inference result. The information of interest can also be referred to as region of interest. Details on information of interest (region of interest), and on calculation methods thereof, will be explained in detail below.

On the basis of the first information of interest and the (2-1)th to (2-N)th information items of interest, the determination unit 110 determines relatedness between the first information of interest and the (2-1)th to (2-N)th information items of interest. The presentation unit 112 presents reference information of the first inference result, on the basis of the relatedness determined by the determination unit 110.

At least some of the units of the information processing apparatus 100 illustrated in FIG. 1 may be implemented in the form of independent devices. Alternatively, the units they may be embodied in the form of software that implements the respective functions. In the present embodiment the units are implemented in the form of respective software.

Figure 2:
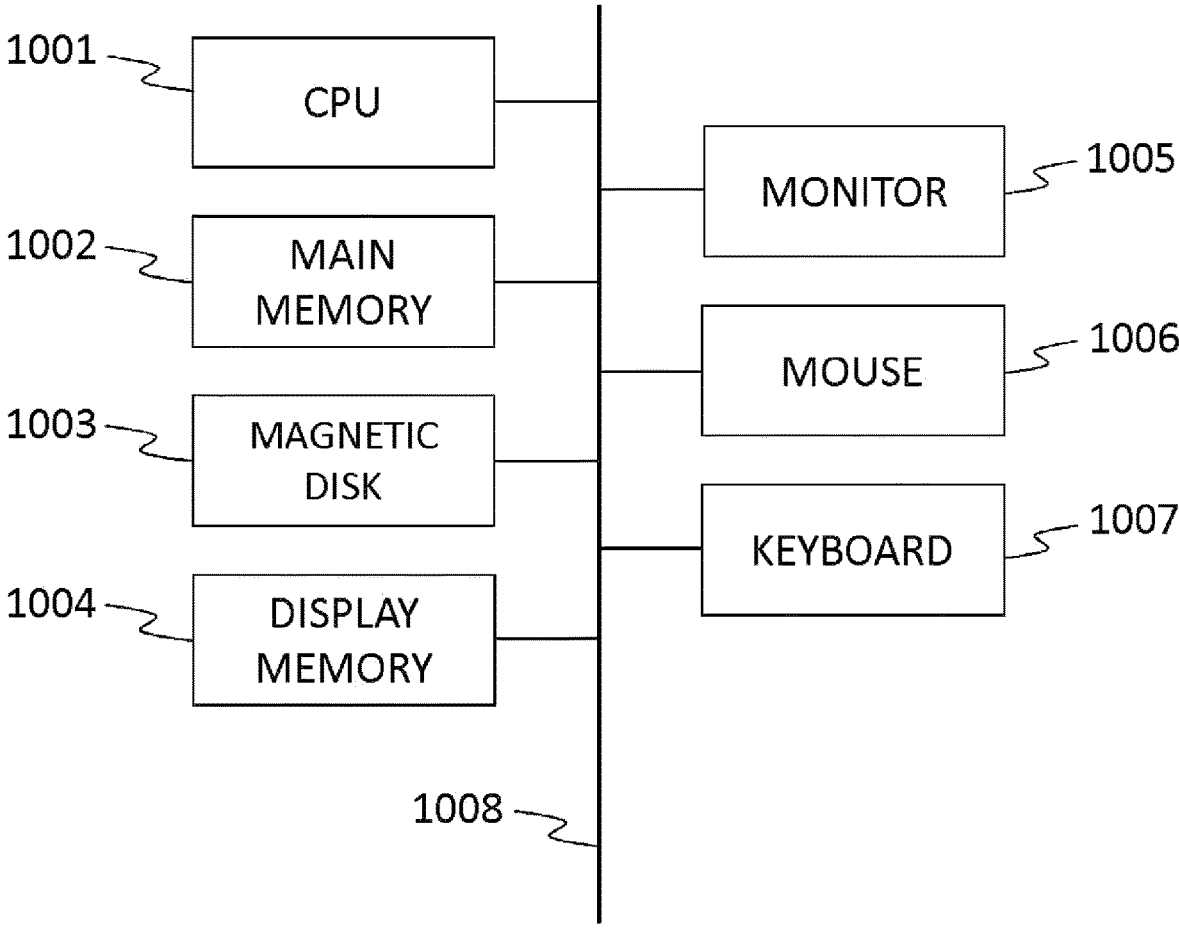
FIG. 2 is a diagram illustrating an example of the hardware configuration of an information processing apparatus.

FIG. 2 is a diagram illustrating an example of the hardware configuration of the information processing apparatus 100.

Herein a CPU 1001 is a processor that mainly controls the operation of each constituent element. A main memory 1002 stores a control program executed by the CPU 1001, and provides a work area for execution of programs by the CPU 1001. A magnetic disk 1003 stores an operating system (OS), device drivers of peripheral devices, and programs for implementing various application software including programs for performing the below-described processes. The CPU 1001 executes the programs stored in the main memory 1002 and the magnetic disk 1003, to thereby implement the functions (software) of the information processing apparatus 100 illustrated in FIG. 1, and the process in the flowcharts described below.

A display memory 1004 temporarily stores display data. A monitor 1005 is for instance a CRT monitor, or a liquid crystal monitor, and displays for instance images and text on the basis of data from the display memory 1004. A mouse 1006 and a keyboard 1007 are used for pointing inputs and for character inputs, respectively, by a user. The constituent elements described above are communicably connected to each other via a common bus 1008.

Figure 3:
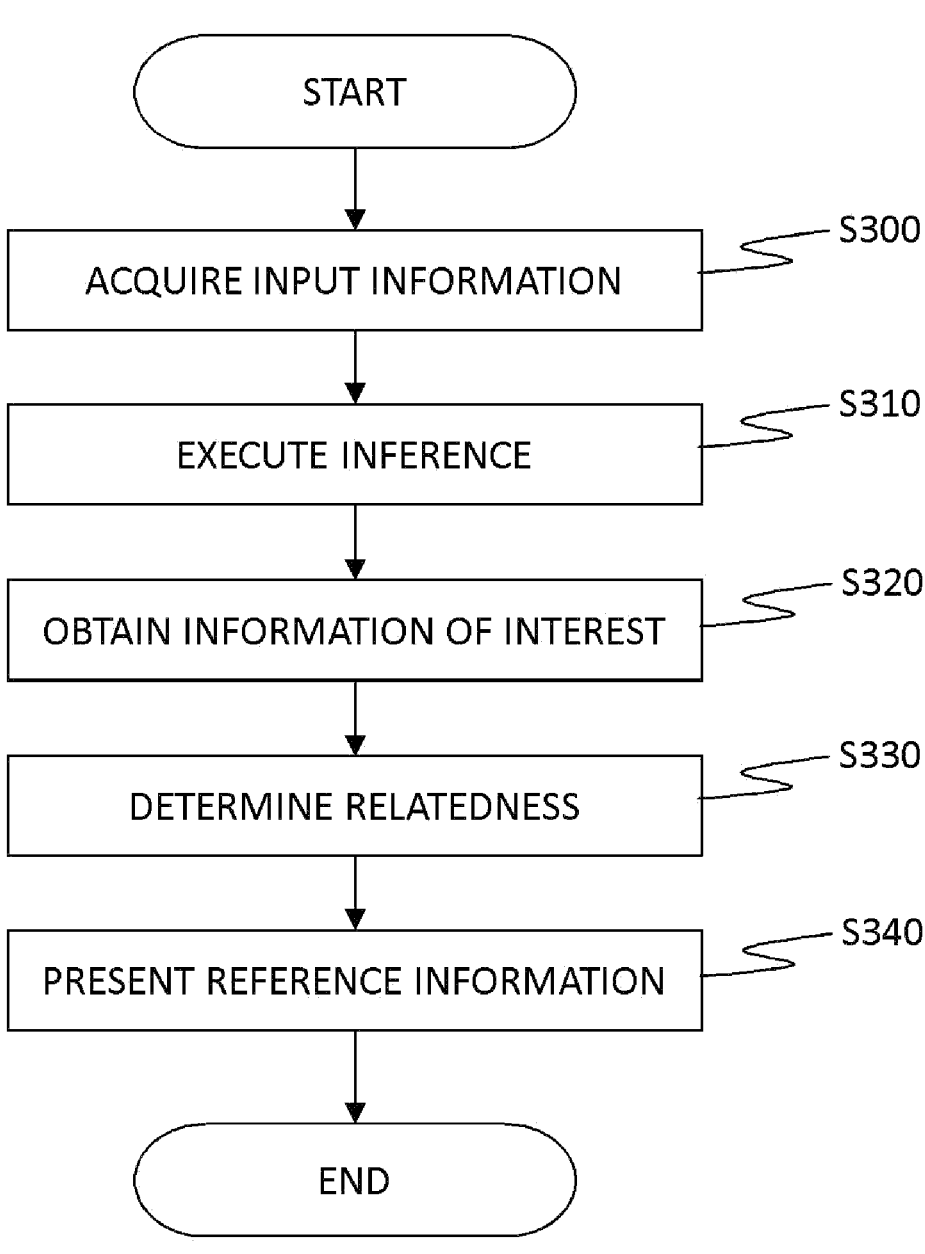
FIG. 3 is a flowchart illustrating an example of processing performed by an information processing apparatus.

The overall processing performed by the information processing apparatus 100 will be explained next with reference to the flowchart in FIG. 3. FIG. 3 is a flowchart illustrating an example of processing performed by the information processing apparatus 100. In the present embodiment the CPU 1001 executes programs, stored in the main memory 1002, that implement the functions of the various units, to thereby realize the processing illustrated in FIG. 3.

In step S300 the acquisition unit 102 requests the storage unit 200 to acquire input information to be used for inference. In the present embodiment a three-dimensional chest X-ray CT image is acquired, as described above.

In step S310 the first inference unit 104 and the second inference units 106-1 to 106-N make inferences on the basis of the input information, and calculate the first inference result and the (2-1)th to (2-N)th inference results, respectively.

In the present embodiment the first inference unit 104 infers a lung disease name using the three-dimensional chest X-ray CT image as input information. The second inference units 106-1 to 106-N infer respectively different image findings (verbal representations of the condition of lung depicted in the medical image). The inference result in each image finding is represented by a binary value denoting whether that finding exists or not. The inference targets (content of information inferred from the input information) of the first inference and the second inference are thus related, but different. In the present embodiment all inference units utilize a convolution neural network (CNN), which is an instance of deep learning. In the present embodiment the structure of the CNN is not particularly limited, except for the input information and the shape of an input layer. For instance all inference units may have the same structure (for instance layer configuration, convolution size and number of kernels); alternatively, some or all of the inference units may have dissimilar or different structures.

To calculate the first inference result and a (2-1)th inference result to a (2-N)th inference result, in step S320 the information-of-interest calculation unit 108 calculates the first information of interest and the (2-1)th to (2-N)th information items of interest. The information of interest in the present embodiment represents the degree of the influence that each pixel in the image data, which is the input information, exerts on the inference result. For instance weights (numerical values) that are assigned to pixels of the three-dimensional chest X-ray CT image, which is the input information, in accordance with the method (Grad-CAM) disclosed by Ramprasaath et al., 2016, serve herein as the information of interest. Specifically, input information is inputted to the inference units, inference results and convolutional layer information are acquired, and error backpropagation is performed on the inference results, to thereby to calculate the gradients of the convolutional layers, whereupon the information of interest is worked out on the basis of the gradients. Note that, technically, the term "pixel" is used for a 2-D image and the term "voxel" is used for a 3-D image, but in this disclosure the term "pixel" is used for both a 2-D and 3-D image.

The means for calculating information of interest is not limited to this method, and other methods may be resorted to. For instance there may be used a method resulting from developing/modifying Grad-CAM, or the method disclosed by Xu et al., "Show, Attend and Tell: Neural Image Caption Generation with Visual Attention", CoRR, arXiv (http://arxiv.org/abs/1502.03044), 2015. Another method will also be described further on in Embodiment 3.

In step S330 the determination unit 110 determines relatedness between the first information of interest and the (2-1)th to (2-N)th information items of interest on the basis of the first information of interest and the (2-1)th to (2-N)th information items of interest. In the present embodiment cosine similarity is calculated through conversion of the weights assigned to the pixels into a one-dimensional weight vector, such that relatedness is determined to arise in a case where a degree of similarity exceeds a threshold value.

Cosine similarity, which is given by the expression below, takes on a value from 0 to 1. The closer the value is to 1, the more similar two given vectors are.

$$Sim(A, B) = \cos\theta = \frac{\vec{A} \cdot \vec{B}}{|\vec{A}||\vec{B}|} \tag{1}$$

Determination of relatedness is not limited to this method, and other methods may be resorted to. For instance mutual information or a correlation ratio may be calculated, and relatedness may be determined on the basis of these values. Other methods will be described further on in Embodiments 2 and 3.

In step S340 the presentation unit 112 presents reference information about the first inference result, on the basis of the relatedness determined by the determination unit 110. As reference information there are presented a second inference result determined to exhibit the highest degree of relatedness (i.e. highest degree of similarity), information of interest of the second inference result, and the first information of interest. The underlying reason for presenting the second inference result as reference information is that if the pieces of information of interest at the time of inference are similar, this suggests that the inference was made by focusing on similar information, and that the first inference result and the second inference result are very likely related. The number of second inference results presented as reference information need not necessarily be one. Herein there may be presented the top M degrees of similarity, or there may be displayed all second inference results determined to exhibit relatedness, or there may be presented the top M second inference results determined to exhibit relatedness. The first information of interest, and the second information of interest determined to be related, may be visualized and be displayed in an image format. The number M is not particularly limited so long as it is an appropriate number suited to system requirements.

Figure 4:
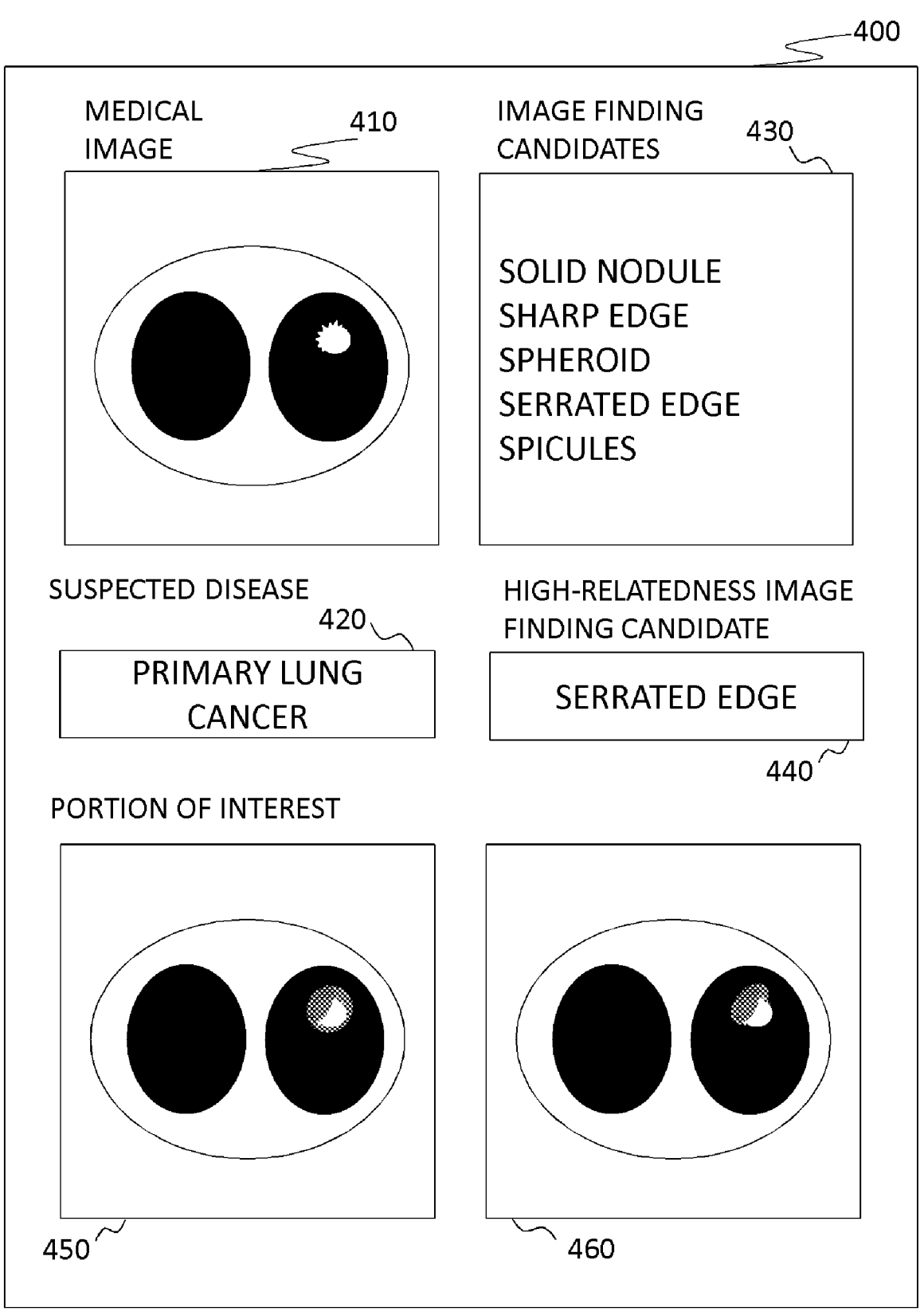
FIG. 4 is a diagram illustrating an example of presentation information.

FIG. 4 is an example of information presented by the presentation unit 112. Presentation information 400 includes a medical image (input information) 410, a diagnosis name 420 as the first inference result, and image findings 430 as the (2-1)th to (2-N)th inference results. As the image findings 430 there are displayed only image findings having a high probability (inference probability) of existence from among image findings inferred in the (2-1)th to (2-N)th inferences. The presentation information 400 further includes an image finding candidate 440. The image finding candidate 440 is a second inference determined to exhibit the highest relatedness. The presentation information 400 further includes a portion of interest made up of information 450 resulting from imaging of the information of interest of the first inference result, and information 460 resulting from imaging of the information of interest of the image finding candidate of highest relatedness (second inference result). Herein only the image finding candidate of highest relatedness is presented, but there may be presented a plurality of image finding candidates. A configuration may be adopted in which information of interest of the image finding candidate selected by the user from among image finding candidates 440 is visualized and displayed.

The information of interest is visualized through rounding of a negative weight (gradient) portion to 0, conversion of weight values to a heat map format, and display of the result superimposed on an original image. Needless to say, imaging may be accomplished in accordance with another method, or alternatively just a heat map alone may be displayed, without superimposed display. An example of display without imaging will be described further on in Embodiment 3.

In the present embodiment a three-dimensional chest X-ray CT image (medical image) is acquired as input information, and the first inference of inferring a diagnosis name, and (2-1)th to (2-N)th inferences resulting from inferring image findings, are made using the medical image as an input. Relatedness between the first inference result and the (2-1)th to (2-N)th inference results is derived by determining the relatedness of information of interest, through acquisition and comparison of the information of interest focused upon at the time of inference. Lastly, the second inference result determined to exhibit relatedness, and information of interest of the second inference result presented with the first inference result, are visualized and presented to the user, as reference information. As a result, the user can compare the information of interest in a simple manner, and can easily determine relatedness between the first inference result (diagnosis name) and the second inference result that is presented. Since the existence of relatedness is inferred by focusing on similar sites, it is deemed that the second inference result (image finding) is a basis for inference of the first inference result (diagnosis name). The user can better grasp thus the first inference, since the first inference result (diagnosis name) is presented along with the inference basis.

Embodiment 2

The information processing apparatus 100 according to Embodiment 2 differs from to that of Embodiment 1 in that herein the input information is a general image, and the input layers (input image size) of the first inference unit 104 and of the second inference units 106-1 to 106-N are different from each other.

The functional configuration and hardware configuration of the information processing apparatus 100 in the present embodiment are identical to those in FIG. 1 and FIG. 2 of Embodiment 1, although some operations are different. The explanation below deals mainly with components that perform operations different from those of Embodiment 1.

In the present embodiment the second inference units 106-1 to 106-N generate divisional information resulting from dividing the input information acquired by the acquisition unit 102, make a second inference using the generated divisional information as inputs, and integrate the results, to thereby calculate (2-1)th to (2-N)th inference results. As in Embodiment 1, the first inference unit 104 makes a first inference on the basis of the whole of the input information, and calculates a first inference result.

Figure 5:
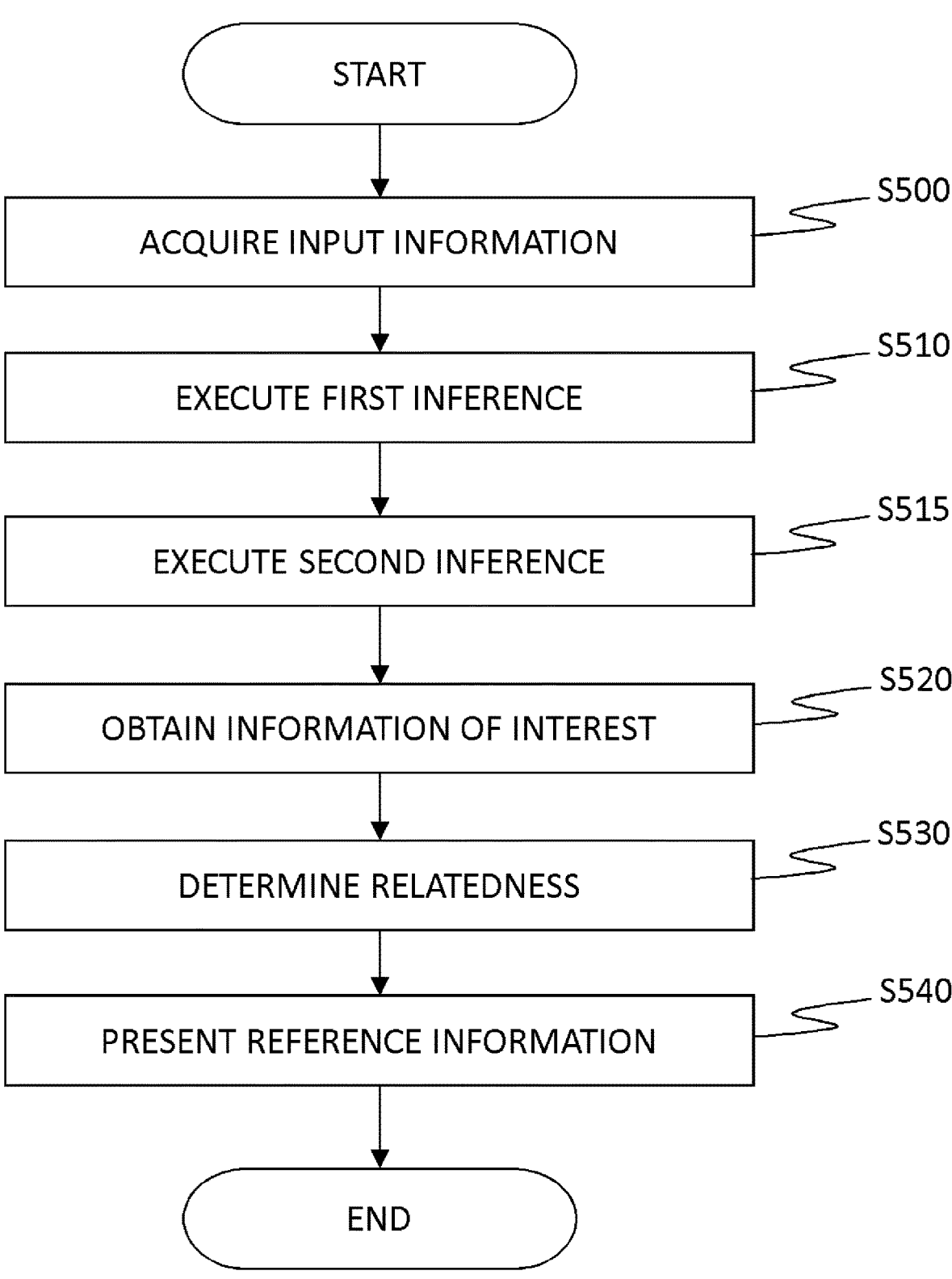
FIG. 5 is a flowchart illustrating an example of processing performed by an information processing apparatus.

The overall processing performed by an information processing apparatus 500 will be explained hereafter with reference to the flowchart in FIG. 5.

In step S500 the acquisition unit 102 requests the storage unit 200 to acquire a natural image.

In step S510 the first inference unit 104 makes an inference on the basis of the input information, and calculates a first inference result. In the present embodiment, the first inference unit 104 classifies the acquired natural image into categories (for instance eagle, hawk, duck, snake or lizard).

In step S515 the second inference units 106-1 to 106-N generate divisional information resulting from dividing the input information, make a second inference using the generated divisional information as inputs, and integrate the results, to calculate (2-1)th to (2-N)th inference results. The divisional information is an image of a divisional region resulting from dividing the natural image, which is the input information. The second inference units 106-1 to 106-N can thus make inferences for more limited inputs, through inference on the basis of divisional information (divisional regions). In terms of images, it is thus possible to make inferences for more localized parts of an image. In a conceivable case, for instance, the second inference unit is ainferencer that infers the presence or absence of a "wing". In this case it is deemed that the presence or absence of a "wing" can be better inferred by making an inference through input of a small image containing only a "wing" portion and a small image not containing a "wing" portion, rather than by inferring the presence or absence of a "wing" through input of a global image containing an "eagle" or a "hawk".

In the present embodiment the divisional information denotes M patch images created by moving the natural image by a certain window size ($W_{window}$, $H_{window}$) and a certain stride size ($X_{stride}$, $Y_{stride}$). The window size is an input layer (image size) of the second inference unit. In the present embodiment the window edge is caused to be aligned with the image edge in a case where the window juts beyond the image upon striding of the window. Needless to say the invention is not limited to this method, and filling with a pixel value 0 may be adopted in a case where the window juts out. Herein there holds $M=\text{ceil}((W-W_{window})/X_{stride}+1)\times\text{ceil}((Y-Y_{window})/Y_{stride}+1)$, with (W, H) as the size of the natural image. Further, ceil( ) denotes a ceiling function that returns an integer value rounded up to the nearest whole number. All sizes are represented by integers, such that there hold $W\geq W_{window}$, $H\geq H_{window}$, $W_{window}\geq X_{stride}>0$ and $H_{window}\geq Y_{stride}>0$.

The window sizes and stride sizes in respective second inference units 106 need not match each other. In other words, the divisional information may differ between second inference units 106. In the present embodiment the pieces of divisional information in the second inference units are set to be identical.

Each of the second inference units 106 integrates the inference results obtained with divisional information as the input, and calculates (2-1)th to (2-N)th inference results. As an example of integration there can be outputted a representative value, for instance a maximum value, mode or average value, or a value obtained by combining some of the foregoing, of inference probability for a case of inference through input of each divisional information. In the present embodiment a maximum value (i.e. the maximum value of the probability of inferring "presence" in all the divisional information) of an instance of inference using an image patch (divisional information) as an input is used as the inference result of the second inference unit.

To calculate the first inference result and the (2-1)th inference result to (2-N)th inference result, in step S520 the information-of-interest calculation unit 108 calculates the first information of interest and the (2-1)th to (2-N)th information items of interest, which are information focused upon in the input information.

The first information of interest may be calculated in accordance with the same method as in Embodiment 1; however, in the present embodiment the information of interest is calculated through inference in a first inferncer, for each piece of divisional information, through the use of the of the (2-1)th to (2-N)th inference units, relying on the technique disclosed in Yasuhiko TACHIBANA et al., *Development of Useful Pretreatment Software for the Use of Convolutional Deep Neural Networks in Diagnostic Imaging, the* 36*th Annual Meeting of the Japanese Society of Medical Imaging Technology,* 2017. Specifically, the importance of each window is determined on the basis of a difference between the inference probability of an instance where an inference is made through masking of an input natural image, at a certain window size, and an inference probability of an instance where inference is made using the original image. All regions of a window of high importance (importance higher than a threshold value) are then calculated as the first information of interest.

The (2-1)th to (2-N)th information items of interest are calculated in the form of a portion of an image patch (region within an image) for which an inference probability at the time of the second inference exceeds a threshold value.

In step S530 the determination unit 110 determines the first information of interest and the (2-1)th to (2-N)th information items of interest on the basis of the first information of interest and the (2-1)th to (2-N)th information items of interest. In the present embodiment the above relatedness is determined on the basis of an inclusion relation between the first information of interest and the (2-1)th to (2-N)th information items of interest. It can also be construed that the determination unit 110 determines the relatedness between the pixels that constitute the first information of interest and the pixels that constitute the (2-1)th to (2-N)th information items of interest.

For instance relatedness can be determined on the basis of an inclusion ratio of the first information of interest (image region) in the second information of interest (image region). An inclusion ratio $I_k$ is given by the expression below, where A is the first information of interest and $A_k$ is (2-k)th information of interest.

$$I_k = \frac{|A \cap A_k|}{|A_k|} \quad (2)$$

Herein $|A_k|$ is the number of pixels in the (2-k)th information of interest $A_k$ and $|A \cap A_k|$ is the number of overlapping pixels of the first information of interest A and the (2-k)th information of interest $A_k$. In a case where $I_k$ exceeds a threshold value it is determined that there is relatedness between the first information of interest and the (2-k)th information of interest.

Processing in step S540 is identical to processing in step S340 of Embodiment 1. In imaging of the information of interest, A may be visualized (superimposed) for the first information of interest, and $A_k$ for the second information of interest. The region $A \cap A_k$ may be further visualized (superimposed) for the purpose of emphasizing the inclusion relation.

Figure 6:
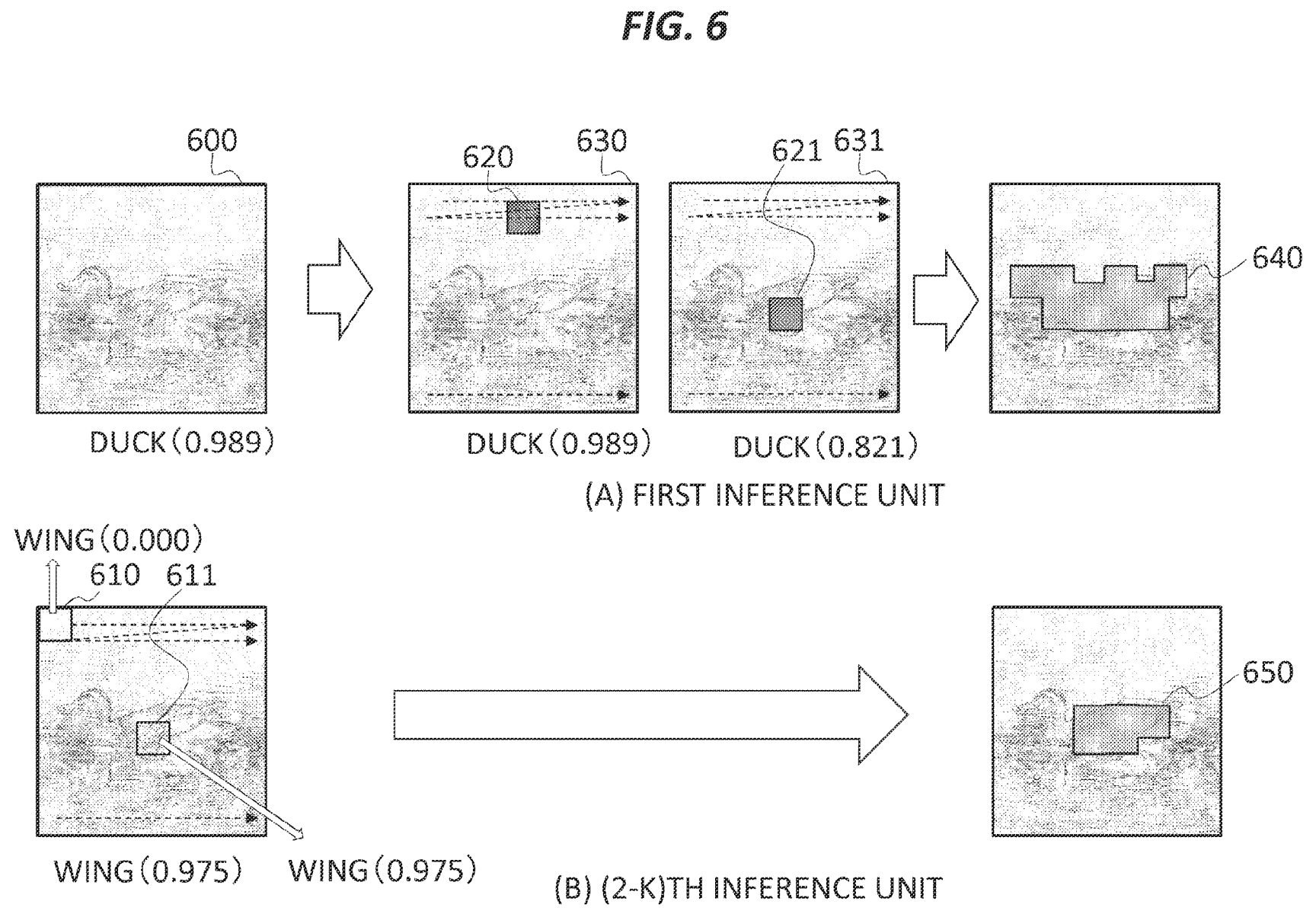

FIG. 6 is a diagram for explaining processing in steps S510 to S530 of the present embodiment.

Firstly, a first inference is made on the basis of the whole of a natural image 600, which is input information, and for instance "duck" is calculated as the first inference result (step S510). The inference probability of "duck" is herein 0.989.

A window is next moved with respect to the input information, to generate patch images which are divisional information, and the second inference is made for each of the patch images. A second inference result is then calculated using a maximum value of the inference probability obtained for the patch images (step S515). For instance "wing" is calculated as a (2-k)th inference result. As an example, herein the inference probability that a "wing" is present in the patch image 610 is 0.000, and the inference probability that a "wing" is present in patch image 611 is 0.975. Given that the inference probability 0.975 of the patch image 611 is the maximum value of inference probability for all patch images, the inference probability of the second inference result is accordingly 0.975.

The inference probability of "duck" is next calculated using the first inferencer for natural images 630, 631 resulting from moving a window of the same size as before and masking of part of the image. The importance of each mask is calculated on the basis of the difference between the inference probability obtained herein and the inference probability obtained in the first inference, and an region of the natural image overlapping a high-importance mask is calculated as first information of interest 640. For instance, inference probabilities when multiplied by masks 620, 621 are 0.989 and 0.821, respectively, and hence differences with respect to the inference probability of 0.989 of an instance without masks are 0 and 0.168, respectively. An region in which this difference exceeds a first threshold value (for instance 0.100) is calculated as the first information of interest 640.

In the second inference, the region of the natural image overlapping the image patch for which an inference probability is obtained that exceeds the second threshold value is calculated as second information of interest 650 (step S520).

Lastly, an inclusion ratio I of the second information of interest 650 is calculated using Expression (2), such that in a case where I exceeds a threshold value, it is determined that the first information of interest 640 and the second information of interest 650 are related (step S530). Expression (2) is a value denoting the ratio of regions (pixels) in the second information of interest 650 that are shared by the first information of interest 640 as well. The higher the above ratio, the higher can be regarded to be the relatedness between the first inference and the second inference.

In the present embodiment a natural image is acquired as input information, and there are performed the first inference of making an inference using the natural image as an input, and the (2-1)th to (2-N)th inferences of making an inference using respective pieces of partial information of the natural image as an input. The relatedness of the information of interest is determined through acquisition/comparison of the information of interest focused upon at the time of inference, and is presented to the user. Accordingly, the user can compare in a simple manner the information of interest and can easily determine the relatedness between the first inference result and the presented second inference result, even when the second inference is made using each of the divisional information of the input information.

Variation 1 of Embodiment 2

In the present embodiment the pieces of divisional information in the second inference units are set to be identical, in step S515, but may differ between respective second inference units. In this case the first information of interest in step S520 may be calculated using information corresponding to fixed divisional information, or may be calculated using respective pieces of information corresponding to pieces of divisional information in respective second inference units. The latter approach allows working out more accurately the relatedness of the first information of interest relative to respective pieces of second information of interest.

Embodiment 3

An information processing apparatus 700 according to Embodiment 3 differs from those in Embodiments 1 and 2 in that the information processing apparatus 700 includes, besides images, also category information and numerical information as additional information, and in that Bayesian networks are used herein as the first inference unit 104 and second inference units 106-1 to 106-N.

Figure 7:
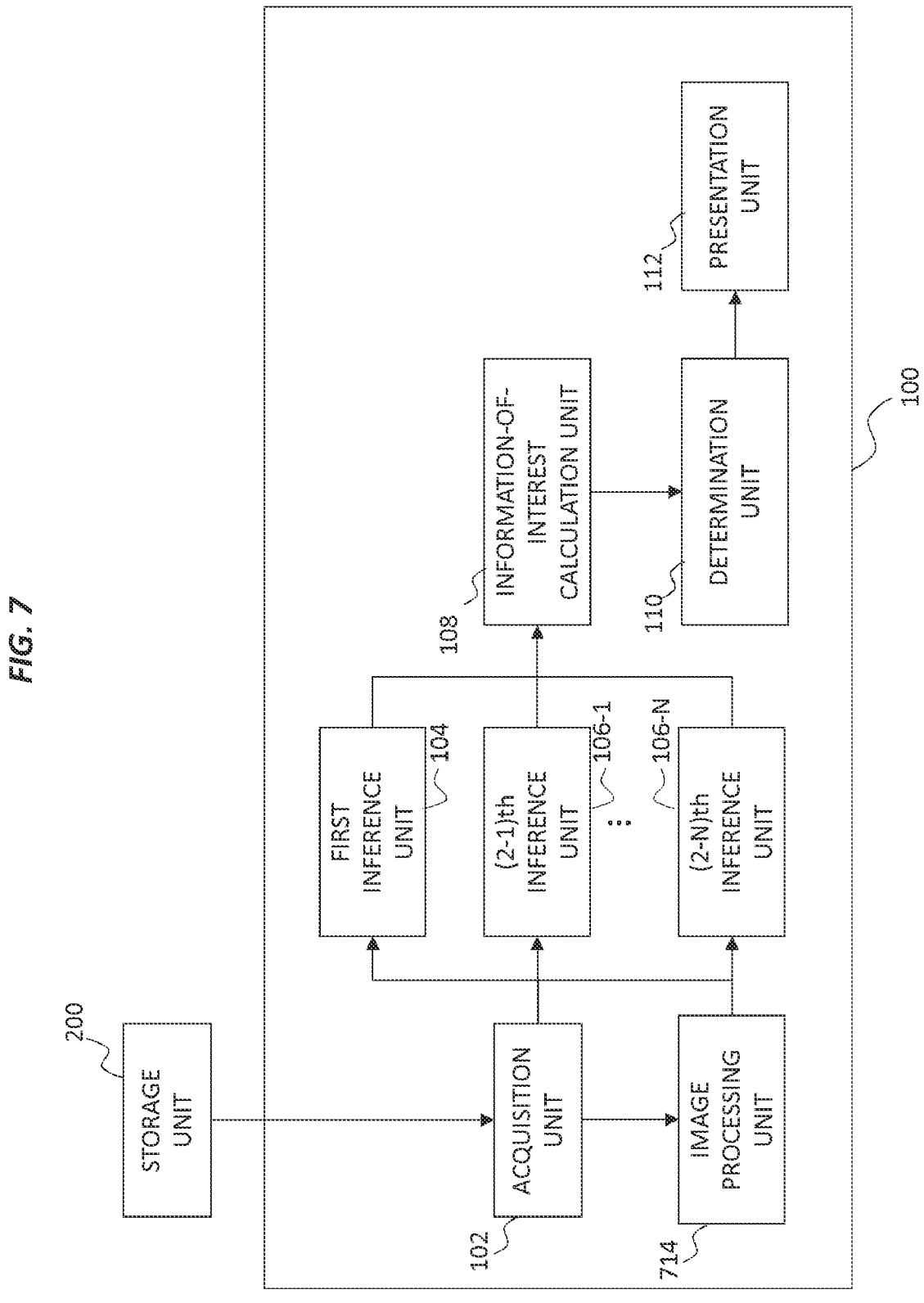
FIG. 7 is a diagram illustrating an example of the functional configuration of an information processing apparatus.

FIG. 7 is a diagram illustrating an example of the functional configuration of the information processing apparatus 700 of the present embodiment. Only differences with respect to Embodiments 1 and 2 will be explained for the components denoted by the same reference symbols as those of FIG. 1.

The information processing apparatus 700 has the acquisition unit 102, an image processing unit 714, the first inference unit 104, the second inference units 106-1 to 106-N, the information-of-interest calculation unit 108, the determination unit 110 and the presentation unit 112. The acquisition unit 102 issues a request to the storage unit 200 and acquires input information (three-dimensional chest X-ray CT image, image findings and clinical information, in the present embodiment). The image processing unit 714 performs image processing on the three-dimensional chest X-ray CT image, from among the input information, and calculates image feature values. The first inference unit 104 and the second inference units 106-1 to 106-N make inferences on the basis of the calculated image feature value, image findings, and clinical information.

The hardware configuration of the information processing apparatus 700 of the present embodiment is identical to that illustrated in FIG. 2 of Embodiment 1.

Figure 8:
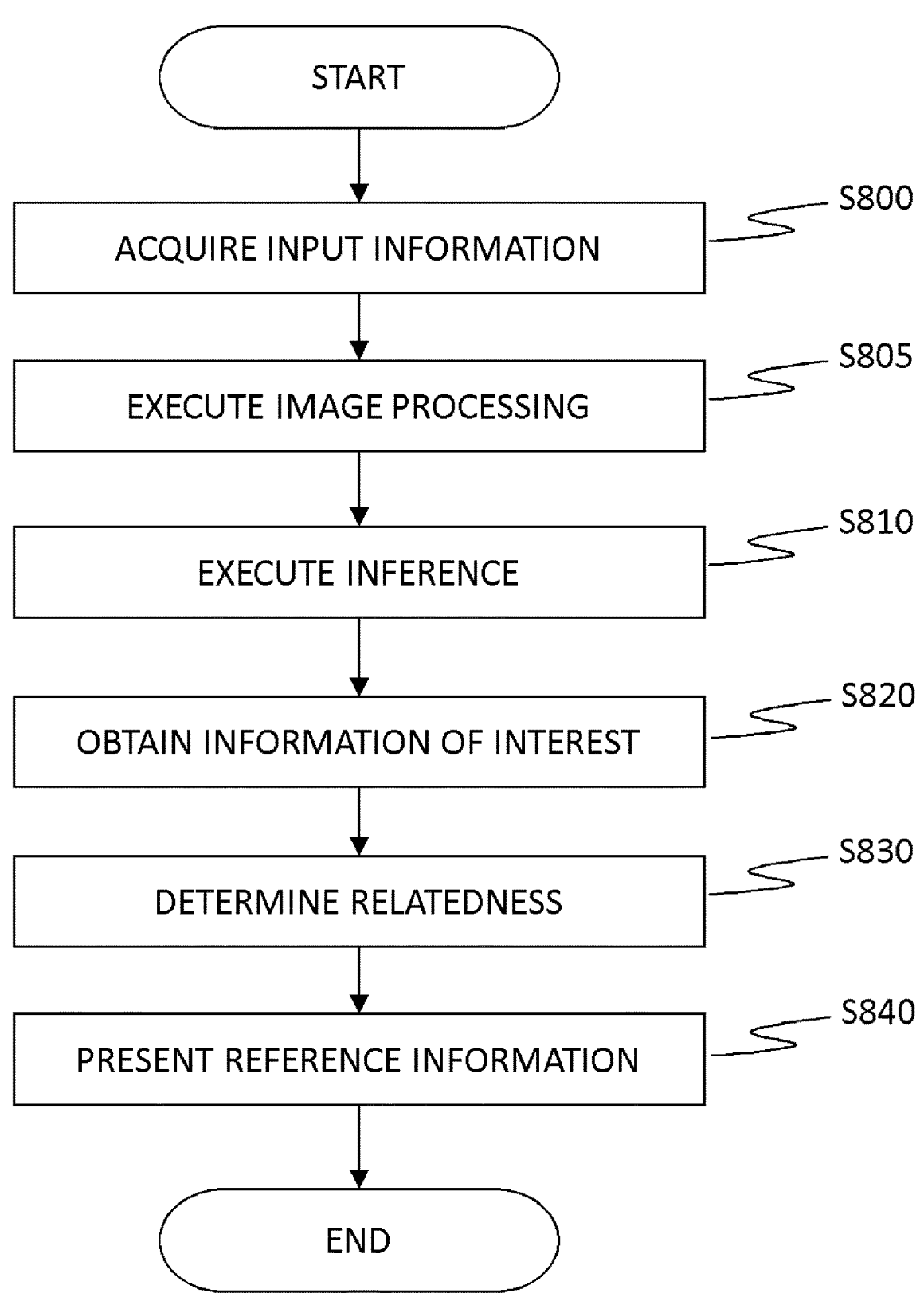
FIG. 8 is a flowchart illustrating an example of processing performed by an information processing apparatus.

The overall processing performed by the information processing apparatus 700 will be explained next with reference to the flowchart in FIG. 8.

In step S800 the acquisition unit 102 requests the storage unit 200 to acquire input information. As pointed out above, the input information in the present embodiment includes a three-dimensional chest X-ray CT image, image findings, as well as category value information and numerical information, as clinical information. The clinical information may be acquired from electronic medical records.

In step S805 the image processing unit 714 makes image processing on the three-dimensional chest X-ray CT image, in an input image, to calculate an image feature value. A known image processing method can be utilized to calculate the image feature value. Examples of image feature values include HOG and SIFT.

In step S810 the first inference unit 104 and the second inference units 106-1 to 106-N make inferences on the basis of the input information, to calculate the first inference result and the (2-1)th to (2-N)th inference results. In the present embodiment the first inference unit 104 infers a lung disease name using, as input information, the image feature value, the inputted image findings and the clinical information. The second inference units 106-1 to 106-N infer image findings that have not been inputted (given), from among the image findings. In the present embodiment all inference units utilize a Bayesian network, as pointed out above. Needless to say, the inference units are not limited thereto, and known methods other than Bayesian networks, for instance probability inference models, neural networks, random forests, XGBoost or the like may be used herein.

To calculate the first inference result and the (2-1)th inference result to (2-N)th inference result, in step S820 the information-of-interest calculation unit 108 calculates the first information of interest and the (2-1)th to (2-N)th information items of interest, which are information focused upon in the input information. In the present embodiment the information of interest is calculated from the input information, in accordance with the method disclosed in Japanese Patent Application Publication No. 2010-200840. Specifically, a degree of support (endorsement) of the inference result is worked out for each piece of input information, whereupon input information having a degree of support higher than a threshold value is determined to be information of interest corresponding to this inference result. For instance, with a degree of support as the difference between the prior probability of an inference result and the posterior probability of the inference result, for case in which there is inputted only certain input information (at least any one from among image feature values, image findings (excluding image findings calculated by the second inference unit) and pieces of clinical information), then input information for which the above degree of support is higher than a threshold value is determined to be information of interest. Thus some of the image feature values, image findings (excluding image findings calculated by the second inference unit) and pieces of clinical information, which are input information, are calculated as the information of interest.

In step S830 the determination unit 110 determines relatedness between the first information of interest and the (2-1)th to (2-N)th information items of interest on the basis of the first information of interest and the (2-1)th to (2-N)th information items of interest. In the present embodiment it is determined that the first information of interest and the (2-1)th to (2-N)th information items of interest are related in a case where the number of overlapping contents of the foregoing exceeds a threshold value.

Processing in step S840 is identical to processing in step S340 of Embodiment 1.

In the present embodiment image findings, and also category information and numerical information as clinical information, are acquired, besides images, as input information, and a first inference and (2-1)th to (2-N)th inferences are performed. The relatedness of the information of interest is determined through acquisition/comparison of the information of interest focused upon at the time of inference, and is presented to the user. As a result the user can compare information of interest in a simple manner, and can easily determine the relatedness between the first inference result and the presented second inference result, also when inferences are made using inputs other than images.

Variation 1 of Embodiment 3

In the present embodiment category information and numerical information are handled as input information, apart from images, but other information may be handled as inputs. For instance text information or audio information may be handled as inputs. In this case a hidden Markov model (HMM), an RNN (Recurrent Network) being one instance of deep learning, or LSTM (Long-Short Term Memory) derived from RNN, may be used as a inferencers.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-198306, filed on Dec. 7, 2021, which is hereby incorporated by reference herein in its entirety.

What is claimed is:

1. An information processing apparatus for performing inferences using medical image data, comprising:
at least one processor configured to:
perform a first inference using the medical image data to obtain a first inference result, wherein the first inference result corresponds to a disease name;
perform a second inference different from the first inference, using the medical image data, to obtain a second inference result, wherein the second inference result corresponds to presence or absence of an image finding;
obtain a first region of interest which is region information focused in the medical image data to obtain, the first inference result corresponding to the disease name, and to obtain a second region of interest which is region information focused upon in the medical image data to obtain, the second inference result corresponding to the presence or absence of the image finding; and
determine relatedness between the first region of interest and the second region of interest.

2. The information processing apparatus of claim 1, wherein the first inference and the second inference are performed using at least one of a category value and a numerical value, in addition to the medical image data.

3. The information processing apparatus of claim 1, wherein the first inference and the second inference are performed using at least one of text information and audio information, in addition to the medical image data.

4. The information processing apparatus of claim 1, wherein the first region of interest and the second region of interest represent a degree of influence that pixels or voxels in the image data exert on the first inference result and the second inference result.

5. The information processing apparatus of claim 4,
wherein the first inference and the second inference are performed using a convolution neural network; and
wherein the first region of interest and the second region of interest are based on weights assigned to pixels, by analyzing the convolution neural network.

6. The information processing apparatus of claim 5, wherein the at least one processor is further configured to determine the relatedness of the first region of interest and the second region of interest on the basis of at least any one from among a degree of similarity, mutual information, correlation ratio, inclusion and overlap, of the first region of interest and the second region of interest.

7. The information processing apparatus of claim 1,
wherein the at least one processor is further configured to obtain the first inference result by performing the first inference on the basis of a whole of medical image data; and
the at least one processor is further configured to perform the second inference on the basis of respective pieces of divisional information resulting from dividing the medical image data, and to obtain the second inference result through integration of inference results for the divisional information.

8. The information processing apparatus of claim 7,
wherein the divisional information is an image of a respective divisional region resulting from dividing the medical image data; and
wherein the first region of interest and the second region of interest are the divisional regions.

9. The information processing apparatus of claim 8, wherein the at least one processor is further configured to determine the relatedness of the first region of interest and the second region of interest, on the basis of a ratio of an image region which is the first region of interest, in an image region which is the second region of interest.

10. The information processing apparatus of claim 1,
wherein the first inference and the second inference are performed using additional information, in addition to the medical image data;
wherein the first inference and the second inference are performed on the basis of the medical image data and the additional information, using a probability inference model; and
wherein the first region of interest and the second region of interest are additional information for which a degree of support of the first inference result and the second inference result, respectively, is higher than a threshold value.

11. The information processing apparatus of claim 10, wherein the additional information includes any one of an image feature value, an image finding and clinical information, of the medical image data.

12. The information processing apparatus of claim 10, wherein the at least one processor is further configured to determine the relatedness of the first region of interest and the second region of interest on the basis of the number of overlapping contents in the first region of interest and the second region of interest.

13. The information processing apparatus of claim 1, the at least one processor is further configured to present reference information of the first inference result; and to present the second inference result, as the reference information, in a case where the at least one processor determines that the first region of interest and the second region of interest are related.

14. The information processing apparatus of claim 13, wherein the at least one processor is further configured to present at least one of the first region of interest and the second region of interest, as the reference information.

15. The information processing apparatus of claim 14, wherein the at least one processor is further configured to present, as the reference information, a second inference result for a second inference in which a degree of relatedness between the first region of interest and the second region of interest is higher than a threshold value, and a second region of interest for a second inference in which a degree of relatedness between the first region of interest and the second region of interest is highest.

16. The information processing apparatus of claim 14, wherein the first region of interest and the second region of interest are further configured to represent a degree of influence that each pixel in the medical image data exerts on the first inference result and the second inference result; and the at least one processor is further configured to present at least one of the first region of interest and the second region of interest in image format.

17. The information processing apparatus of claim 1, wherein the first inference and the second inference are performed using an image finding or clinical information of the medical image, in addition to the image data.

18. An information processing apparatus of claim 1, wherein the at least one processor is further configured to determine the relatedness by determining a relatedness between pixels that constitute the first region of interest and pixels that constitute the second region of interest.

19. An information processing method for performing an inference using image data, comprising:

a first inference step of making a first inference using the medical image data to obtain a first inference result, wherein the first inference result corresponds to a disease name;

at least one second inference step of performing a second inference different from the first inference, using the medical image data, to obtain a second inference result, wherein the second inference result corresponds to presence or absence of an image finding;

an information-of-interest acquisition step of obtaining a first region of interest which is region information focused in the medical image data to obtain the first inference result corresponding to the disease name, and obtaining a second region of interest which is region information focused in the medical image data to obtain the second inference result corresponding to the presence or absence of the image finding; and a determination step of determining relatedness between the first region of interest and the second region of interest.

20. A computer readable medium that non-transitorily stores a program for causing an information processing apparatus to execute an information processing method that includes:

a first inference step of performing a first inference using the medical image data to obtain a first inference result, wherein the first inference result corresponds to a disease name;

at least one second inference step of performing a second inference different from the first inference, using the medical image data, to obtain a second inference result, wherein the second inference result corresponds to presence or absence of an image finding;

an information-of-interest acquisition step of obtaining a first region of interest which is region information focused in the medical image data to obtain the first inference result corresponding to the disease name, and obtaining a second region of interest which is region information focused in the medical image data to obtain the second inference result corresponding to the presence or absence of the image finding; and a determination step of determining relatedness between the first region of interest and the second region of interest are related.

21. An information processing apparatus for performing inferences using image data, comprising:

at least one processor configured to:

perform a first inference using the image data to obtain a first inference result;

make a second inference different from the first inference, using the image data, to obtain a second inference result;

obtain a first region of interest which is region information focused in the image data to obtain the first inference result, and to obtain a second region of interest which is region information focused upon in the image data to obtain the second inference result; and determine relatedness between the first region of interest and the second region of interest, wherein the first inference and the second inference are performed using additional information, in addition to the image data;

wherein the first inference and the second inference are performed on the basis of the image data and the additional information, using a probability inference model; and wherein the first region of interest and the second region of interest are additional information for which a degree of support of the first inference result and the second inference result, respectively, is higher than a threshold value.

22. An information processing method for performing an inference using image data, comprising:

a first inference step of making a first inference using the image data to obtain a first inference result;

at least one second inference step of making a second inference different from the first inference, using the image data, to obtain a second inference result;

an information-of-interest acquisition step of obtaining a first region of interest which is region information focused in the image data to obtain the first inference result, and obtaining a second region of interest which is region information focused in the image data to obtain the second inference result; and a determination step of determining relatedness between the first region of interest and the second region of interest, wherein the first inference and the second inference are performed using additional information, in addition to the image data;

wherein the first inference and the second inference are performed on the basis of the image data and the additional information, using a probability inference model; and wherein the first region of interest and the second region of interest are additional information for which a degree of support of the first inference result and the second inference result, respectively, is higher than a threshold value.

\* \* \* \* \*